United States Patent [19]

Eibl et al.

[11] Patent Number: 5,274,081
[45] Date of Patent: Dec. 28, 1993

[54] COMPLEX SUITABLE FOR CARRYING OUT A METHOD OF PURIFYING PRE-S HEPATITIS B SURFACE ANTIGEN

[75] Inventors: Johann Eibl; Friedrich Dorner, both of Vienna; Artur Mitterer, Orth/Donau, all of Austria

[73] Assignee: Immuno A.G., Vienna, Austria

[21] Appl. No.: 789,743

[22] Filed: Nov. 8, 1991

Related U.S. Application Data

[62] Division of Ser. No. 578,939, Sep. 7, 1990, abandoned.

[30] Foreign Application Priority Data

Sep. 20, 1989 [AT] Austria .................. 2198/89

[51] Int. Cl.$^5$ .................. C07K 3/12; C07K 17/00; A61K 39/12; C12N 7/02
[52] U.S. Cl. .................. 530/413; 530/412; 530/402; 530/403; 530/362; 530/363; 530/364; 530/350; 424/89; 435/239
[58] Field of Search .......... 530/362, 363, 350, 413, 530/412, 402, 403; 435/239; 424/89

[56] References Cited

U.S. PATENT DOCUMENTS

| | | | |
|---|---|---|---|
| 3,947,352 | 3/1976 | Cuatrecasas et al. | 210/692 |
| 3,976,767 | 8/1976 | Neurath | 424/89 |
| 4,046,871 | 9/1977 | Reckel | 530/363 |
| 4,087,519 | 5/1978 | Trepo | 424/86 |
| 4,123,427 | 10/1978 | Daniel | 530/389.5 |
| 4,168,300 | 9/1979 | Anderson et al. | 436/514 |
| 4,181,713 | 1/1980 | McAleer et al. | 530/380 |
| 4,225,487 | 9/1980 | Cuatrecasas et al. | 530/362 |
| 4,352,884 | 10/1982 | Nakashima et al. | 435/180 |
| 4,411,832 | 10/1983 | Cuatrecasas et al. | 530/363 |
| 4,489,167 | 12/1984 | Ochi et al. | 436/518 |
| 4,579,661 | 4/1986 | Gustafsson et al. | 210/635 |
| 4,683,136 | 7/1987 | Milich et al. | 424/89 |
| 4,707,542 | 11/1987 | Friedman et al. | 530/371 |
| 4,742,158 | 5/1988 | Lehman et al. | 530/371 |
| 4,816,564 | 3/1989 | Ellis et al. | 530/350 |
| 4,847,080 | 7/1989 | Neurath et al. | 424/89 |
| 4,855,055 | 8/1989 | Lin et al. | 210/635 |
| 4,861,588 | 8/1989 | Neurath et al. | 424/89 |
| 4,959,323 | 9/1990 | Acs et al. | 435/252.33 |
| 5,011,915 | 4/1991 | Yamazaki | 530/414 |
| 5,019,386 | 5/1991 | Machida et al. | 424/89 |
| 5,030,720 | 7/1991 | Bertland, II et al. | 530/413 |

FOREIGN PATENT DOCUMENTS

| | | |
|---|---|---|
| 0243103 | 4/1987 | European Pat. Off. |
| 0341733 | 11/1989 | European Pat. Off. |
| 2530247 | 1/1976 | Fed. Rep. of Germany |
| 464154 | 7/1973 | U.S.S.R. |

OTHER PUBLICATIONS

Ishihara et al., J. Med. Vir. 21(1):89-95. 1988.
Ise et al., "Interaction of Hepatitis B Surface Antigen with Serum Albumin of Various Species on Polystyrene Latex Beads", Med. Microbiol. Immunol., 176:199-208 (1987).
Xuanyong et al., "The Interaction Between Native Serum Albumin and Hepatitis B Virus", Arch. Virol., 98:163-170 (1988).

Primary Examiner—Christine M. Nucker
Assistant Examiner—Chris Dubrule
Attorney, Agent, or Firm—Foley & Lardner

[57] ABSTRACT

There is disclosed a complex comprised of an insoluble polymer carrier to which monomeric human albumin is covalently bound and of a pre-S hepatitis B surface antigen bound in an elutable form to the monomeric human albumin by its pre-S(2)- and/or pre-S(1)-region. This complex may be used for therapeutic and diagnostic purposes and enables the rapid and efficient purification of pre-S-HBsAg by affinity chromatography.

13 Claims, No Drawings

COMPLEX SUITABLE FOR CARRYING OUT A METHOD OF PURIFYING PRE-S HEPATITIS B SURFACE ANTIGEN

This application is a divisional of Ser. No. 07/578,939, filed Sep. 7, 1990, now abandoned.

The invention relates to a complex comprised of an insoluble polymer carrier to which human albumin is covalently bound and of a pre-S hepatitis B surface antigen (pre-S-HBsAg) as well as to a method for the purification of pre-S-HBsAg.

From EP-A2-0 243 103, a method of purifying pre-S-HBsAg is known, which consists in disrupting yeast cells expressing recombinant pre-S-HBsAg and separating pre-S-HBsAg from the cell contents by affinity chromatography. Polymerized human serum albumin (polyalbumin) covalently bound to a matrix serves as the adsorbent for pre-S-HBsAg. This polyalbumin is a product synthetically prepared in a high-molecular form by cross-linking agents, e.g., glutaraldehyde. The pre-S-HBsAg is adsorbed on the polyalbumin by its pre-S(2)-region and, after having washed off interfering substances, is eluted from the matrix and subjected to a secondary purification step.

It was evidenced that an efficient polyalbumin receptor existed in the pre-S region of HBsAg, which is composed of a polypeptide including 55 amino acids and encoded by a section of the hepatitis virus DNA immediately preceding the S-region ("pre-S2") (Valenzuela et al., Bio/Technology Vol. 3: 317-320, 1985). Furthermore, it was demonstrated that both this immediately preceding region (pre-S2) and the total pre-S-region, in connection with the S-region (pre-S1), encode surface proteins that constitute receptors to hepatitis B virus (HBV) for the binding to cell membranes of liver cells.

HBsAg that contains a pre-S region for the first time was obtained from infected human plasma in 1979 (Neurath and Strick, Arch. Virol., 60: 79-81, 1979) and later on was produced also by way of genetic engineering by Valenzuela et al. (Bio/Technology 3: 317, 1985, and Nature 311: 67, 1984) and Paoletti et al. (PNAS 81: 193, 1984).

Subsequently, various recombinantly expressed pre-S-containing surface antigens were suggested as vaccines to induce the formation of antibodies against HBV. These antibodies are directed against the receptor of the virus, thus preventing its binding to the liver cell and the infection involved.

The purification of the antigens by affinity chromatography through polyalbumin has the disadvantage that impurities, yet even toxic substances, such as glutaraldehyde, are introduced into the eluate due to the use of cross-linking agents in the production of polymerization products.

It is the object of the present invention to eliminate this difficulty and to provide a complex which, in addition to the opportunity of a rapid and efficient affinity chromatographic purification of pre-S-HBsAg, offers new applications for therapeutic and diagnostic purposes.

The complex according to the invention is comprised of an insoluble polymer carrier based, in particular, on agarose or dextrane, to which monomeric human albumin is covalently bound, and of a pre-S hepatitis B surface antigen bound in an elutable form to the monomeric human albumin by its pre-S(2)- and/or pre-S(1)-region.

It was found according to the invention that pre-S-HBsAg would be complexed to the monomeric human albumin to an extent sufficient for affinity chromatographic purification only if the latter were covalently bound to the carrier. If the albumin merely binds by way of adsorption, the pre-S-HBsAg can be complexed to the albumin not at all or only extremely slightly such that an affinity chromatographic purification will not be possible. Another advantage of the complex according to the invention consists in that pre-S-HBsAg may be readily eluted, the protein thus being recoverable in a more gentle manner and a greater yield.

An insoluble polymer carrier to which monomeric human albumin is covalently bound is required for the formation of the complex of the invention. This insoluble polymer carrier, thus, also falls within the scope of the invention. To produce the insoluble polymer carrier according to the invention, any polymer capable of covalently binding proteins upon suitable activation may be used. The following carrier substances may be used:

organic polymers, such as polyamides and vinyl polymers (polyacrylamide, polystyrene and polyvinyl alcohols and derivatives thereof), as well as natural polymers, such as cellulose, dextrane, agarose, chitin and polyamino acids, and inorganic polymers, such as silica gel, glass and metal hydroxides.

These carrier substances may be used in the form of particles, e.g., as molecular sieves, in the form of membranes or of plates, e.g., as microtiter plates.

Preferably, the insoluble polymer carrier is based on agarose or dextrane.

The complex according to the invention is storable over extended periods of time, i.e., both in the aqueous phase in which the carrier is present in the swollen state (e.g., as an affinity resin) and in the lyophilized state (e.g., as a membrane or a microtiter plate). Lyophilization, preferably, is carried out in a volatile buffer containing glycine or glucose.

Pre-S-HBsAg can be isolated from the complex according to the invention in high purity. The invention also relates to the use of the complex according to the invention for the preparation of diagnostics and vaccines, the vaccines being applicable both for active immunization against hepatitis B and for obtaining specific immunoglobulin of donors immunized with such vaccines.

The carrier according to the invention may be loaded with pre-S hepatitis B surface antigen in a simple manner by contacting an aqueous solution of hepatitis B surface antigen with the carrier, the pre-S-containing fractions of the hepatitis surface antigens being selectively adsorbed on the albumin molecules.

The method according to the invention for the purification of pre-S hepatitis B surface antigen by using a complex according to the invention is characterized in that the complex is washed with a buffer solution to remove possibly present impurities, and the pre-S hepatitis B surface antigen selectively adsorbed on the monomeric human albumin is cleaved and recovered either by treating the complex with an eluting agent containing chaotropic substances, such as urea, guanidine hydrochloride, thiocyanate, potassium chloride, magnesium chloride or potassium iodide; or by treating the complex with detergents; or by treating the complex with a pH modifying agent; whereupon a secondary purification step is carried out, if necessary.

A preferred embodiment of the method according to the invention is characterized in that ionic detergents, in particular sodium desoxycholate and taurodesoxycholic acid, or zwitterionic detergents, in particular 3[(3-cholamidopropyl)-dimethyl-ammonio]-1-propane sulfonate and 3[(3-cholamidopropyl)-dimethyl-ammonio]-2-hydroxy-1-propane sulfonate, or non-ionic detergents, in particular octyl glucopyranosides, may be used as the detergents.

It has proved that the quarternary structure of the eluted pre-S-HBsAg is not affected when using these detergents.

Preferably, the secondary purification step after elution comprises gel filtration, ultracentrifugation, hydrophobic chromatography, lectin affinity chromatography or ion exchange chromatography. Any of these purification steps yields pre-S-HBsAg in a purity greater than 90%.

The invention will be explained in more detail in the following:

The pre-S-HBsAg can be expressed from recombinant vaccinia virus that contains the genetic information of the pre-S-HBsAg. This technique has been described in the literature (Moss et al., Nature 311: 67 (1984)).

At first, a high-titer virus stock of recombinant vaccinia virus was prepared by infecting vero cells with 1 PFU/cell. After 2 to 3 days of incubation at 37° C. the infected cells are shaken into the medium and pelleted by centrifugation at 5,000 g for 20 min. The supernatant is poured off and stored at 4° C. The cells are washed three times in PBS, whereupon a trypsin solution is added to the cell suspension until a final concentration of trypsin of 0.025% by mass is reached. After this, the suspension is gently stirred at 37° C. for 30 min, pooled with the supernatant, aliquoted into ampoules and deep-frozen at −80° C. By this method, the virus titer is increased by approximately ten times as compared to that usually obtained in cell medium.

A vero cell inoculum is prepared by passaging cells in plastic Roux and Roller bottles (Nunc) in order to produce sufficient cells to be able to inoculate a 6-liter fermenter, which, in turn, serves as the inoculum for a 40-liter vessel. To this end, a single ampoule of vero cells of a defined passage number at first is thawed and passaged to provide 12 confluent Roller bottles.

The cells are trypsinized, resuspended in medium 199 with 5% by mass of foetal calf serum and mixed with a suspension of microcarriers (Cytodex 3, Pharmacia) and pumped into the fermenter to give a final concentration of $2 \times 10^8$ cells and 5 g microcarrier per liter. At this stage, additional medium is added in an amount of one third of the final working volume.

The cells are allowed to adhere to the microcarriers for a period of three hours while slowly stirring the suspension. After this, further medium (DMEM containing 5% by mass of fetal calf serum) is added in order to obtain the final working volume. As soon as a cell density of 6 to $8 \times 10^8$/liter has been achieved, a continuous perfusion with DMEM (containing 5% by mass of fetal calf serum) is started. Upon achievement of a cell density of approximately $5 \times 10^9$/liter, the microcarriers are trypsinized and the cells with the microcarriers are pumped into the 40-liter fermenter, which contains additional 5 g microcarrier per liter. Upon adsorption, the fermenter is filled to a volume of 40 liters and cultivation proceeds as described above.

When a cell density of $5 \times 10^9$/liter has been reached, the medium is pumped off after the microcarriers have settled. Five liters of the medium containing the recombinant microorganism are pumped into the fermenter so as to give a m.o.i.-value of about 2 PFU per recombinant cell. After adsorption of the virus, the fermenter is filled with medium 199 (containing 5% by mass of fetal calf serum) to a volume of 40 liters and is perfused with 40 liters of the same medium for 40 hours. After this period of time, about 80% of the cells has detached from the microcarriers and is pumped off together with the medium.

The remaining cells still adhering to the microcarriers are detached therefrom by washing with medium under rapid stirring and are pumped off and pooled with the first fraction. The microcarriers are removed by means of a 70 um sieve. By centrifugation in a Beckmann JFC-Z continuous flow rotor, the cells are pelletized at 16,000 g. The medium is concentrated by ultrafiltration in the Pellikon system (Millipore-Waters). Urea is added to the concentrated medium until an 8M solution adjusts. This solution is dialyzed.

The concentrated vero cell supernatant is added to a column packed with an insoluble polymer carrier substance to which human serum albumin is covalently bound. The coupling method is known to depend on the chemical nature of the carrier. When using Sepharose, activation is effected with CNBr, for instance, whereupon the monomeric human serum albumin is coupled this activated Sepharose.

After washing of the column with buffer 1 consisting of 0.2M sodium acetate (pH 4.0) and 0.5M NaCl, with buffer 2 consisting of 0.1M Tris (pH 8.0) and 0.5M NaCl, with a solution 3 consisting of 8M urea, and finally with buffer 3 consisting of 0.02M Tris (pH 7.4), the vero cell supernatant is applied to the column. As soon as the supernatant has been adsorbed by the column, the non-adsorbed proteins are washed from the column with buffer 4 consisting of 0.02M Tris (pH 7.4) and 0.5M NaCl. The adsorbed pre-S(2)-HBsAg is eluted with sodium thiocyanate in buffer 4 (1 to about 4M, preferably 3M) at a pH of from 6 to about 8, preferably at pH 7 (buffer 5) or with 8M urea in buffer 4, preferably with 4M urea (buffer 6). This separation according to the invention with monomeric human albumin results in a 145-fold enrichment of pre-S-HBsAg. Its identity is revealed by the immunoblotting technique (Burnette, Anal. Biochem., 112, 195, 1981) and by silver stained polyacrylamide gels (silver staining; Morrissey, Anal. Biochem., 117, 307, 1981), the purity amounting to at least 80%.

The pre-S(2)-HBsAg may be further purified, i.e., by gel filtration on Sepharose (Pharmacia). In doing so, the fraction obtained above is dialyzed against a buffer consisting of 0.02M Tris (pH 7) and applied to the Sepharose column activated with 0.02M Tris (pH 7). The purity of the pre-S-HBsAg can be shown to be greater than 90% by silver staining and immunoblotting.

The realization of the method according to the invention is further illustrated by the following exemplary embodiments.

EXAMPLE 1

Purification of pre-S(2)-HBsAg by monomeric human albumin affinity chromatography The recombinant vaccinia virus with the generic information for the pre-S(2)-HBsAg was obtained using the techniques described by Moss et al. (Nature 311: 67, 1984). The high-titer stock of the recombinant vaccinia virus was prepared as described above. The vero cells for infection with the recombinant virus were grown under the same conditions as described above. The concentrated dialyzed medium with the pre-S(2)-HBsAg was obtained in the previously described manner.

Monomeric human albumin was covalently bound to CNBr-activated Sepharose 4B (Pharmacia) following the manufacturer's instructions. After this, a column was packed with a volume of 50 ml matrix and washed with 500 ml of buffer solution 1, 500 ml of buffer solution 2, 500 ml of solution 3 and, finally, 500 ml buffer solution 4.

The clarified vero cell supernatant contained 8500 mg protein and 95 mg pre-S(2)-HBsAg and was pumped onto the prepared column at a flow rate of 100 ml/hour. When the total amount had entered the column, the non-adsorbed proteins were washed from the column with buffer solution 4. The pre-S(2)-HBsAg was eluted with 3M sodium thiocyanate, pH 7 (buffer solution 5). Identification and purity analysis were effected by silver staining and immunoblotting following polyacrylamide gel electrophoresis.

Duplicate aliquots of the fractions eluted from the column were incubated for 15 min at 100° C. in a buffer consisting of 2% by mass of sodium dodecyl sulfate (SDS), 0.125M Tris-HCl (pH 6.8) and 100 mM dithiotreitol. The samples were electrophoresed through 12.5% by mass polyacrylamide separating gel for 2.5 hours at 65 mA/gel (Laemmli, Nature 227: 680, 1971). One set of the gel samples was stained with silver nitrate to visualize the polypeptides. The other set of the samples was assayed by immunoblotting, using rabbit antiserum.

The eluted fractions contained 42 mg protein and 68 mg pre-S(2)-HBsAg. Thus, a 145-fold enrichment of the pre-S(2)-HBsAg had been achieved.

The following Examples 2 and 3 illustrate the secondary purification of the fractions obtained in Example 1.

EXAMPLE 2

A pre-S(2)-HBsAg-containing solution obtained according to Example 1 was further purified by column chromatography on Sepharose 4B (Pharmacia). At first, the column was prepared and washed with 500 ml 0.02M Tris (pH 7.0) at a flow rate of 30 ml/hour. The pre-S(2)-HBsAg-containing solution was dialyzed against this buffer, and the dialyzed antigen present at a concentration of 10 mg/12 ml in addition to 6.2 mg protein/12 ml was added to the column. The column was activated with 0.02M Tris (pH 7.0) and the eluted pre-S(2)-HBsAg-containing fraction contained 4.8 mg protein and 8.2 mg pre-S(2)-HBsAg. Silver-staining and immunoblotting of the polyacrylamide gels carried out in the manner described in Example 1 revealed a purity of the pre-S(2)-HBsAg greater than 90%.

EXAMPLE 3

A pre-S(2)-HBsAg-containing solution obtained according to Example 1 was further purified by column chromatography on lentil-lectin Sepharose 4B (Pharmacia). At first, the column was prepared and washed with 100 ml 0.02M Tris (pH 7.0) at a flow rate of 50 ml/hour. The pre-S(2)-HBsAg-containing solution was dialyzed against this buffer, and the dialyzed antigen present at a concentration of 21 mg/25 ml in addition to 13 mg protein/25 ml was applied onto the column at a flow rate of 25 ml/hour. After this, the non-adsorbed material was washed off with Tris buffer solution and the pre-S(2)-HBsAg was eluted with Tris buffer solution containing 5% by mass of alphamethylmannoside. The eluate contained 9.1 mg protein and 15.6 mg pre-S(2)-HBsAg. Silver staining and immunoblotting of the polyacrylamide gels were carried out as described in Example 1 and revealed a purity of the pre-S(2)-HBsAg greater than 90%.

The purification of hepatitis B surface antigens bearing the pre-S(1)-region instead of the pre-S(2)-region or pre-S(2)- and pre-S(1)-regions is accomplished in a manner analogous to the exemplary embodiments described. The method according to the invention may, indeed, be used to purify any protein that carries a pre-S(1)- and-/or a pre-S(2)-region of HBsAg.

The following Examples 4 to 6 describe the use of various carrier substances and forms as well as coupling methods that serve the required purpose of use.

EXAMPLE 4

Coupling of monomeric human albumin to silicate carriers

Possible carriers are silica gels or glass microbeads (controlled pore glass beads=CPG).

10 g of an aminated glass carrier (aminopropyl CPG, Pierce) are shaken with 100 ml of a 2.5% aqueous glutaraldehyde solution for four hours at room temperature. Upon activation, the carrier is thoroughly washed free from aldehyde with deionized water. The thus activated carrier is incubated with 200 mg human serum albumin in 0.1M phosphate buffer (pH 8.0) for one hour. After blocking with 1M ethanolamine and thorough washing with phosphate buffer, the carrier is ready for use.

200 ml of a pre-S(2)-HBsAg-containing cell culture supernatant (11 mg pre-S(2)-HBsAg, 950 mg protein) are incubated with 10 ml of the affinity carrier for two hours at 14° C. Unbound protein is removed by washing with a buffer on a sintering suction filter and the specifically bound pre-S(2)-HBsAg is eluted by incubation of the packed carrier in 10 ml 8M urea solution. This assay yielded 6.8 mg highly pure pre-S(2)-HBsAg at an overall protein amount of 5.4 mg (determination according to Bradford).

EXAMPLE 5

Coupling of monomeric human albumin to membranes

Membranes, e.g., of nylon, polyvinylidene difluoride or cellulose polyacrylamide mixed polymers are possible carriers. Nylon membrane (e.g., Zetabind, CUNO) is partially hydrolyzed by incubation in HCl/H$_2$O. The released amino groups are reacted with 1M oxaldialdehyde in the presence of 0.1M sodium cyanoborohydride at pH 7 for two hours. After washing with deionized water, human serum albumin (10 mg/ml in 0.1M phosphate buffer pH 7) is coupled to this membrane activated with reactive aldehyde groups in the presence of 0.1M sodium cyanoborohydride. Excess reactive groups are blocked by the addition of 1M ethanolamine. After washing with phosphate buffer (0.1M; pH 8), the membrane may be used to selectively bind pre-S(2)-containing proteins.

The binding capacity of a thus produced membrane is 5 to 10 ug pre-S(2)-HBsAg/cm$^2$.

EXAMPLE 6

Coupling of a monomeric human albumin to microtiter plates

To this end, functionalized polystyrene plates, such as, e.g., Amino-Plate (including primary amino groups) or Carbo-Plate (including carboxyl groups) (Nissho Iwai Corp., Tokyo) or similar materials may be used.

200 ul of a solution of N-ethoxycarbonyl-2-ethoxy-1,2-dihydro-quinoline (40 mM in 50% aqueous ethanol) are pipetted into each well of a 96-well microtiter plate and incubated for two hours at 40° C. After careful washing with ethanol and deionized water, 200 ul of a 1% aqueous solution of human serum albumin are each pipetted into a well and incubated at +4° C. over night. After blocking with 1M ethanolamine or 1M acetate buffer pH 4 and subsequent washing, the plate is ready for use.

100 ul of a pre-S(2)-HBsAg-containing cell culture supernatant are pipetted into the prepared microtiter plate in increasing dilutions and incubated at +4° C. for two hours. After washing with buffer and incubation with enzyme-labeled anti-pre-S(2)-HBsAg (monoclonal antibodies) following the known ELISA technique, the bound portion of pre-S(2)-protein is determined by substrate addition according to known methods of absorption spectroscopy.

If the microtiter plate is loaded with SH-denaturized pre-S(2)-HBsAg or synthetic pre-S(2)-peptide, a thus treated plate may be used for assaying anti-pre-S(2)-antibodies (e.g., from patients' sera).

10 mg pre-S(2)-HBsAg in 10 ml phosphate buffer (0.1M; pH 7.0) are incubated with 100 myl mercaptoethanol in 10% sodium dodecyl sulfate (SDS) for 5 min at 100° C. In doing so, the immunologically active S-antigen of HBsAg is destroyed (Milich D. R. et al., Enhanced Immunogenicity of the Pre-S-Region of Hepatitis B Surface Antigen, Science 227: 1195-1199 (1985)). After blocking of the SH-groups with 500 mg iodoacetamide for one hour, excess reaction products are eliminated by dialysis and the pre-S(2)-antigen is diluted to 100 ul protein/ml with phosphate buffer pH 7.4.

A prepared HSA microtiter plate is coated with this pre-S(2) solution and subsequently washed. Thus prepared plates may be stored even in the dry state.

100 ul of an anti-pre-S(2)-containing rabbit serum are each pipetted into the wells in increasing dilutions. After incubation at +4° C. over night, bound pre-S(2)-antibodies are assayed by means of absorption spectroscopy by incubation with enzyme-labeled anti-rabbit serum and subsequent substrate addition.

EXAMPLE 7

Binding capacity and yield of pre-S(2)-HBsAg when using various albumin carrier complexes Human serum albumin (HSA) and polymerized human serum albumin (poly-HSA) were covalently and adsorptively bound to various carrier substances in comparable amounts. The binding capacity and the yield of pre-S(2)-HBsAg after elution were determined by means of a HBsAg-specific ELISA method and are summarized in the following Table:

| Albumin | Carrier | Type of bond | Capacity mg/g gel | % yield after elution with | | | |
|---|---|---|---|---|---|---|---|
| | | | | 2M U | 4M U | 8M U | 3M KSCN |
| monomeric | CNBr-Sepharose | covalent via NH$_2$ | 7.6 | 45 | 85 | 60 | 50 |
| monomeric | anti-HSA Sepharose | adsorptive | 0 | — | — | — | — |
| polymeric | anti-HSA Sepharose | adsorptive | 5.8 | — | — | — | — |
| polymeric | CNBr-Sepharose | covalent via NH$_2$ | 6.4 | 12 | 40 | 55 | 45 |

U = Urea

It is apparent from the Table that higher yields of pre-S(2)-HBsAg are obtained with the insoluble polymer carrier according to the invention, with which the monomeric human albumin is covalently bound to Sepharose in the present exemplary embodiment, than with Sepharose to which polyalbumin is covalently bound.

These remarkably higher yields are due to the more gentle eluting conditions made possible by employing the carrier of the invention. In addition, it can be seen that it is only the covalent binding of HSA to the carrier that results in the inventive characteristic of the pre-S(2)-affinity and that a molecular sieve to which albumin is bound merely by adsorption is not suitable for affinity chromatographic purification.

What we claim is:

1. A complex comprised of (i) an insoluble polymer carrier, (ii) monomeric human albumin and (iii) a pre-S hepatitis B surface antigen comprising a pre-S(2)-region, wherein said monomeric human albumin is covalently bound to said carrier and said pre-S hepatitis B surface antigen is bound in an elutable form to said monomeric human albumin by said pre-S(2)-region.

2. A complex as set forth in claim 1, wherein said insoluble polymer carrier is based on a substance selected from the group consisting of agarose and dextrane.

3. A method of purifying pre-S hepatitis B surface antigen by using a complex comprised of an insoluble polymer carrier, monomeric human albumin, and a pre-S hepatitis B surface antigen comprising a pre-S(2)-region, wherein said monomeric human albumin is covalently bound to said carrier and said pre-S hepatitis B surface antigen is bound in an elutable form to said monomeric human albumin by said pre-S(2)-region, which method comprises the steps of:
- washing said complex with a buffer solution to remove possibly present impurities and
- eluting said complex and recovering said pre-S hepatitis B surface antigen.

4. A method as set forth in claim 3, wherein said pre-S hepatitis B surface antigen is recovered by treating said complex with an eluting agent containing chaotropic substances.

5. A method as set forth in claim 4, wherein said chaotropic substances are selected from the group consisting of urea, guanuidine hydrochloride, thiocyanate, potassium chloride, magnesium chloride and potassium iodide.

6. A method as set forth in claim 3, wherein said pre-S hepatitis B surface antigen is recovered by treating said complex with a detergent.

7. A method as set forth in claim 3, wherein said pre-S hepatitis B surface antigen is recovered by treating said complex with a pH modifying agent.

8. A method as set forth in claim 3, further comprising a secondary purification step.

9. A method as set forth in claim 6, wherein said detergent is selected from the group consisting of an ionic detergent, a zwitterionic detergent and a non-ionic detergent.

10. A method as set forth in claim 9, wherein said ionic detergent is selected from the group consisting of sodium desoxycholate and taurodesoxycholic acid.

11. A method as set forth in claim 9, wherein said zwitterionic detergent is selected form the group consisting of 3[(3-cholamidopropyl)-dimethyl-ammonio]-1-propane sulfonate and 3[(3-cholamidopropyl)-dimethyl-ammonio]-2-hydroxy-1-propane sulfonate.

12. A method as set forth in claim 9, wherein said non-ionic detergent is octyl glucopyranoside.

13. A method as set forth in claim 8, wherein said secondary purification step comprises a process selected from the group consisting of gel filtration, ultracentrifugation, hydrophobic chromatography, lectin affinity chromatography and ion exchange chromatography.

* * * * *